(12) United States Patent
Zones et al.

(10) Patent No.: US 6,709,644 B2
(45) Date of Patent: Mar. 23, 2004

(54) SMALL CRYSTALLITE ZEOLITE CHA

(75) Inventors: Stacey I. Zones, San Francisco, CA (US); Lun-Teh Yuen, San Francisco, CA (US); Stephen J. Miller, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 331 days.

(21) Appl. No.: 09/943,723

(22) Filed: Aug. 30, 2001

(65) Prior Publication Data

US 2003/0069449 A1 Apr. 10, 2003

(51) Int. Cl.$^7$ .......................... C01B 39/48; C07C 4/00; C07C 209/16; B01D 53/02
(52) U.S. Cl. .................. 423/706; 423/712; 423/716; 423/213.2; 423/213.5; 423/239.2; 95/90; 564/474; 564/479; 585/640
(58) Field of Search .................. 423/706, 712, 423/716, 213.2, 213.5, 239.2; 95/90; 564/474, 479; 585/640

(56) References Cited

U.S. PATENT DOCUMENTS

| 4,544,538 A | | 10/1985 | Zones | |
|---|---|---|---|---|
| 4,737,592 A | | 4/1988 | Abrams et al. | |
| 5,191,141 A | * | 3/1993 | Barger et al. | 585/640 |
| 2003/0104931 A1 | * | 6/2003 | Mertens et al. | 502/214 |

OTHER PUBLICATIONS

Szostak, Handbook of Molecular Sieves, Van Nostrand Reinhold, 1992, pp. 117–124.

Szostak, Handbook of Molecular Sieves, Van Nostrand Reinhold, 1992, pp. 448–449.

* cited by examiner

Primary Examiner—David Sample
(74) Attorney, Agent, or Firm—Richard J. Sheridan

(57) ABSTRACT

The present invention relates to zeolites having the crystal structure of chabazite (CHA) and having small crystallite size, to processes using the small crystallite CHA as a catalyst, and to gas separation processes using the small crystallite CHA.

21 Claims, No Drawings

SMALL CRYSTALLITE ZEOLITE CHA

BACKGROUND OF THE INVENTION

FIELD OF THE INVENTION

The present invention relates to crystalline zeolite SSZ-62 that has the CHA crystal structure, a mole ratio greater than 10 of silicon oxide to aluminum oxide and has a crystallite size of 0.5 micron or less. The present invention also relates to a method for preparing SSZ-62 using specific sources of silicon and aluminum, and a N,N,N-trimethyl-1-adamantammonium cation templating agent, to processes employing SSZ-62 as a catalyst, and to processes using SSZ-62 to separate gasses.

SUMMARY OF THE INVENTION

The present invention is directed to a family of crystalline molecular sieves with unique properties, referred to herein as "zeolite SSZ-62" or simply "SSZ-62". Preferably, SSZ-62 is obtained in its aluminosilicate form. As used herein, the term "aluminosilicate" refers to a zeolite containing both alumina and silica.

In accordance with this invention, there is provided a zeolite having the CHA crystal structure, a mole ratio greater than about 10 of an oxide of a first tetravalent element to an oxide of a second tetravalent element which is different from said first tetravalent element, trivalent element, pentavalent element or mixture thereof and having a crystallite size of 0.5 micron or less.

In accordance with the present invention, there is also provided a zeolite having the CHA crystal structure, a mole ratio greater than about 10 of silicon oxide to aluminum oxide, and having a crystallite size of 0.5 micron or less.

Also provided in accordance with the present invention is a method of preparing a aluminosilicate crystalline material having the CHA crystal structure and a crystallite size of 0.5 micron or less, said method comprising contacting under crystallization conditions an aluminum hydroxide gel dried to about 50 wt. % $Al_2O_3$ with a slight alkalinity and the ability to absorb $CO_2$ and solubilize rapidly in water, precipitated silica with a water content of about 5–15 wt. %, and a templating agent comprising a N,N,N-trimethyl-1-adamantammonium cation.

This invention also provides a process for converting lower alcohols and other oxygenated hydrocarbons comprising contacting said lower alcohol or other oxygenated hydrocarbon under conditions to produce liquid products with a catalyst comprising a zeolite having the CHA crystal structure, a mole ratio greater than about 10 of silicon oxide to aluminum oxide and having a crystallite size of about 0.5 micron or less.

Also provided by the present invention is an improved process for the reduction of oxides of nitrogen contained in a gas stream in the presence of oxygen wherein said process comprises contacting the gas stream with a zeolite, the improvement comprising using as the zeolite a zeolite having the CHA crystal structure, a mole ratio greater than about 10 of silicon oxide to aluminum oxide and having a crystallite size of 0.5 micron or less. The zeolite may contain a metal or metal ions (such as cobalt, copper or mixtures thereof) capable of catalyzing the reduction of the oxides of nitrogen, and may be conducted in the presence of a stoichiometric excess of oxygen. In a preferred embodiment, the gas stream is the exhaust stream of an internal combustion engine.

The present invention further provides a process for producing dimethylamine comprising reacting methanol and/or dimethyl ether and ammonia in the gaseous phase in the presence of a catalyst comprising a zeolite having the CHA crystal structure, a mole ratio greater than about 10 of silicon oxide to aluminum oxide and having a crystallite size of 0.5 micron or less.

Further provided by the present invention is an improved process for separating gasses using a membrane containing a zeolite, the improvement being the use in the membrane of a zeolite having the CHA crystal structure, a mole ratio greater than about 10 of silicon oxide to aluminum oxide and having a crystallite size of 0.5 micron or less.

DETAILED DESCRIPTION OF THE INVENTION

In preparing SSZ-62 zeolites, a N,N,N-trimethyl-1-adamantammonium cation is used as a crystallization template or structure directing agent ("SDA"). In general, SSZ-62 is prepared by contacting an aluminum hydroxide gel dried to about 50 wt. % $Al_2O_3$ with a slight alkalinity and the ability to absorb $CO_2$ and solubilize rapidly in water, precipitated silica with a water content of about 5–15 wt. % with the SDA in an aqueous solution.

SSZ-62 is prepared from a reaction mixture having the composition shown in Table A below. Silicon- and aluminum-containing reactants are expressed as $SiO_2$ and $Al_2O_3$, respectively.

TABLE 1

| | Reaction Mixture | |
|---|---|---|
| | Typical | Preferred |
| $SiO_2/Al_2O_3$ | 20–50 | 25–40 |
| OH—/$SiO_2$ | 0.15–0.40 | 0.25–0.40 |
| Q/$SiO_2$ | 0.10–0.35 | 0.18–0.22 |
| $M_{2/n}/SiO_2$ | 0.05–0.20 | 0.12–0.18 |
| $H_2O/SiO_2$ | 10–25 | 12–20 | where Q is the SDA, M is alkali metal or alkaline earth metal, and n is the valence of M.

In practice, SSZ-62 is prepared by a process comprising:
(a) preparing an aqueous solution containing an aluminum hydroxide gel dried to about 50 wt. % $Al_2O_3$ with a slight alkalinity and the ability to absorb $CO_2$ and solubilize rapidly in water, precipitated silica with a water content of about 5–15 wt. % and a N,N,N-trimethyl-1-adamantammonium cation having an anionic counterion which is not detrimental to the formation of SSZ-62;
(b) maintaining the aqueous solution under conditions sufficient to form crystals of SSZ-62; and
(c) recovering the crystals of SSZ-62.

The source of silicon is precipitated silica with a water content of about 5–15 wt. %. An example of such a material is HiSil 233 available from PPG Industries, Inc.

The source of aluminum is an aluminum hydroxide gel dried to about 50 wt. % $Al_2O_3$. The gel has slight alkalinity and is able to absorb $CO_2$. It is rapidly soluble in water. The aluminum hydroxide has a particle density of less than about 1.0 g/cm$^3$, preferably less than about 0.9 g/cm$^3$, more preferably less than about 0.8 g/cm$^3$ and most preferably in the range of about 0.1 g/cm$^3$ to about 0.8 g/cm$^3$. An example of such a material is Reheis F-2000 available from Reheis Chemical Co.

The aluminum hydroxide, as added to the reaction mixture, further has an average particle size of less than about 40 microns, preferably less than about 25 microns, more preferably less than about 15 microns, still more preferably less than about 10 microns, and most preferably within the range of about 0.1 to 10 microns, with preferably less than about 25% of the particulates having a particle size outside the range of about 0.1 to 40 microns. In a more preferred embodiment, less than about 25%, even more preferably less than 10% of the particles have a particle size outside the range of about 0.1 to about 25 microns.

The aluminum hydroxide gel has a low alkali level before it is added to the reaction mixture. The gel contains less than about 0.12 wt. % and preferably less than 0.10 wt. % alkali. It is most preferred that the gel have an alkali content in the range of about 0.01 wt. % to about 0.10 wt. % where alkali may be one or more of the Group IA elements.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The templating agent may be used to provide hydroxide ion. Thus, it may be beneficial to ion exchange, for example, the halide for hydroxide ion, thereby reducing or eliminating the alkali metal hydroxide quantity required. The alkali metal cation or alkaline earth cation may be part of the as-synthesized crystalline oxide material, in order to balance valence electron charges therein.

The SDA used to prepare SSZ-62 is a N,N,N-trimethyl-1-adamantammonium cation having the following structure:

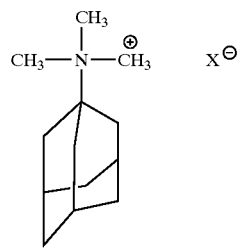

The anion (X⁻) associated with the cation may be any anion which is not detrimental to the formation of the zeolite. Representative anions include halogen, e.g., fluoride, chloride, bromide and iodide, hydroxide, acetate, sulfate, tetrafluoroborate, carboxylate, and the like. Hydroxide is the most preferred anion.

The reaction mixture is maintained at an elevated temperature until the crystals of the SSZ-62 zeolite are formed. The hydrothermal crystallization is usually conducted under autogenous pressure, at a temperature between 100° C. and 200° C., preferably between 135° C. and 160° C. The crystallization period is typically greater than 1 day and preferably from about 3 days to about 20 days.

Preferably, the zeolite is prepared using mild stirring or agitation.

During the hydrothermal crystallization step, the SSZ-62 crystals can be allowed to nucleate spontaneously from the reaction mixture. The use of SSZ-62 crystals as seed material can be advantageous in decreasing the time necessary for complete crystallization to occur. In addition, seeding can lead to an increased purity of the product obtained by promoting the nucleation and/or formation of SSZ-62 over any undesired phases. When used as seeds, SSZ-62 crystals are added in an amount between 0.1 and 10% of the weight of silica used in the reaction mixture.

Once the zeolite crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-62 zeolite crystals. The drying step can be performed at atmospheric pressure or under vacuum.

SSZ-62 as prepared has a mole ratio of silicon oxide to aluminum oxide of greater than 10. SSZ-62 can also be made with a mole ratio of silicon oxide to aluminum oxide of at least 30.

The crystallite size of SSZ-62, as determined by TEM, is less than 0.5 micron, preferably less than 0.1 micron.

Crystalline SSZ-62 can be used as-synthesized, but preferably will be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica to alumina mole ratio. The zeolite can also be steamed; steaming helps stabilize the crystalline lattice to attack from acids.

The zeolite can be used in intimate combination with hydrogenating components, such as tungsten, vanadium molybdenum, rhenium, nickel cobalt, chromium, manganese, or a noble metal, such as palladium or platinum, for those applications in which a hydrogenation-dehydrogenation function is desired.

Metals may also be introduced into the zeolite by replacing some of the cations in the zeolite with metal cations via standard ion exchange techniques (see, for example, U.S. Pat. No. 3,140,249 issued Jul. 7, 1964 to Plank et al.; U.S. Pat. No. 3,140,251 issued Jul. 7, 1964 to Plank et al.; and U.S. Pat. No. 3,140,253 issued Jul. 7, 1964 to Plank et al.). Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the SSZ-62. The zeolite can also be impregnated with the metals, or, the metals can be physically and intimately admixed with the zeolite using standard methods known to the art.

Typical ion-exchange techniques involve contacting the synthetic zeolite with a solution containing a salt of the desired replacing cation or cations. Although a wide variety of salts can be employed, chlorides and other halides, acetates, nitrates, and sulfates are particularly preferred. The zeolite is usually calcined prior to the ion-exchange procedure to remove the organic matter present in the channels and on the surface, since this results in a more effective ion exchange. Representative ion exchange techniques are disclosed in a wide variety of patents including U.S. Pat. No. 3,140,249 issued on Jul. 7, 1964 to Plank et al.; U.S. Pat. No. 3,140,251 issued on Jul. 7, 1964 to Plank et al.; and U.S. Pat. No. 3,140,253 issued on Jul. 7, 1964 to Plank et al.

Following contact with the salt solution of the desired replacing cation, the zeolite is typically washed with water and dried at temperatures ranging from 65° C. to about 200° C. After washing, the zeolite can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of SSZ-62, the spatial arrangement of the atoms which form the basic crystal lattice of the zeolite remains essentially unchanged.

SSZ-62 can be formed into a wide variety of physical shapes. Generally speaking, the zeolite can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded.

SSZ-62 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

Condensation of Alcohols

SSZ-62 can be used to condense lower aliphatic alcohols having 1 to 10 carbon atoms to a gasoline boiling point hydrocarbon product comprising mixed aliphatic and aromatic hydrocarbon. The process disclosed in U.S. Pat. No. 3,894,107, issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst, nor should the exchange be such as to eliminate all acidity. There may be other processes involving treatment of oxygenated substrates where a basic catalyst is desired.

Preparing Dimethylamine

SSZ-62 can also be used as a catalyst to prepare dimethylamine. Dimethylamine is generally prepared in industrial quantities by continuous reaction of methanol (and/or dimethylether) and ammonia in the presence of a silica-alumina catalyst. The reactants are typically combined in the vapor phase, at temperatures in the range of 300° C. to 500° C., and at elevated pressures. Such a process is disclosed in U.S. Pat. No. 4,737,592, issued Apr. 12, 1988 to Abrams et al., which is incorporated by reference in its entirety.

The catalyst, i.e., SSZ-62, is used in its acid form. Acid forms of zeolites can be prepared by a variety of techniques, such as those described above. Preferably, the SSZ-62 used to prepare dimethylamine will be in the hydrogen form, or have an alkali or alkaline earth metal, such as Na, K, Rb, or CS, ion-exchanged into it.

The process of the present invention involves reacting methanol and/or dimethylether and ammonia in amounts sufficient to provide a carbon/nitrogen (C/N) ratio from about 0.2 to about 1.5, preferably about 0.5 to about 1.2. The reaction is conducted at a temperature from about 250° C. to about 450° C., preferably about 300° C. to about 400° C. Reaction pressures can vary from about 7–7000 kPa (1–1000 psi), preferably about 70–3000 kPa (10–500 psi). A methanol and/or dimethylether space time of about 0.01–80 hours, preferably 0.10–1.5 hours, is typically used. This space time is calculated as the mass of catalyst divided by the mass flow rate of methanol/dimethylether introduced into the reactor.

Gas Separation

SSZ-62 can also be used to separate gasses. For example, it can be used to separate carbon dioxide from natural gas. Typically, the SSZ-62 is used as a component in a membrane that is used to separate the gasses.

EXAMPLES

The following examples demonstrate but do not limit the present invention.

Example 1

Synthesis of SSZ-62

In a Teflon cup for a Parr 23 ml stainless steel reactor, a solution is formed by adding 7 grams of a 0.61 M solution of N,N,N-trimethyl-1-adamantammonium hydroxide (prepared as described in U.S. Pat. No. 4,544,538, issued Oct. 1, 1985 to Zones, the disclosure of which is incorporated by reference in its entirety), 0.18 gram of solid NaOH, and 0.112 gram of Reheis F-2000 aluminum hydroxide gel (dried, 50–53 wt. % $Al_2O_3$). After a clear solution is obtained, 1.63 grams of HiSil 233 silica source is stirred in. The reactor is closed and mounted onto a spit operating within a Blue M convection oven. The spit is rotated at 45 RPM and the reaction mixture is heated at 160° C. for six days. Analysis by SEM shows that a product, with very small crystals, seems to have formed. The XRD powder data for this product shows the product to have the chabazite structure with noticeable line broadening over conventional SSZ-13 (also with the chabazite structure). Analysis by TEM shows a large, homogeneous distribution of crystals averaging 0.05 to 0.1 micron on edge. Typical SSZ-13 products have been 0.5 to 1.0 micron in length (the crystals are close to cubic in morphology). The silica/alumina mole ratio of the SSZ-62 product is 22.

Comparative Examples

Some comparative examples are also run using the procedure of Example 1. Using greater or lesser mole ratios of water/silica (ratios of 44, 8, 3.5 as compared with 16 above) results in products with larger crystals. Replacing the HiSil 233 silica source with Cabosil M5 fumed silica available from Cabot Corporation also produces larger crystals.

Example 2

Calcination of SSZ-62

The material from Example 1 is calcined in the following manner. A thin bed of material is heated in a muffle furnace from room temperature to 120° C. at a rate of 1° C. per minute and held at 120° C. for three hours. The temperature is then ramped up to 540° C. at the same rate and held at this temperature for 5 hours, after which it is increased to 594° C. and held there for another 5 hours. A 50/50 mixture of air and nitrogen is passed over the zeolite at a rate of 20 standard cubic feet per minute during heating.

The product of the calcination is analyzed with nitrogen using a Micrometrics Digisorb instrument. The product has a micropore volume of 0.28 cc/g and a surface area of near 700 $m^2/g$.

Example 3

$NH_4$ Exchange

Ion exchange of calcined SSZ-62 material (prepared in Example 2) is performed using $NH_4NO_3$ to convert the zeolite from its $Na^+$ form to the $NH_4^+$ form, and, ultimately, the $H^+$ form. Typically, the same mass of $NH_4NO_3$ as zeolite is slurried in water at a ratio of 25–50:1 water to zeolite. The exchange solution is heated at 95° C. for 2 hours and then filtered. This procedure can be repeated up to three times. Following the final exchange, the zeolite is washed several times with water and dried. This $NH_4^+$ form of SSZ-62 can then be converted to the H⁺ form by calcination (as described in Example 9) to 540° C.

Example 4
Use of SSZ-62 To Convert Methanol

The zeolite of Example 3, after heating to 540° C. to convert $NH_4^+$ to $H^+$, is pelletized at 2–3 KPSI, then crushed and meshed to 20–40. 0.50 Gram is loaded into a ⅜ inch stainless steel reactor tube with alundum on the side of the zeolite bed where the feed is introduced. The reactor is heated in a Lindberg furnace to 1000° F. for 3 hours in air, and then the temperature is reduced to 330° C. in a stream of nitrogen at 20 cc/min. A 22.1% methanol feed (22.1 g methanol/77.9 g water) is introduced into the reactor at a rate of 1.31 cc/hr.

The catalyst gives greater than 90% selectivity for $C_2$–$C_4$ olefins and does not show methanol breakthrough for greater than 15 hours. Prior art catalysts with larger crystallite sizes than SSZ-62 (like SSZ-13 with a crystallite size of about 1.2 microns and a silica/alumina mole ratio of about 9 or 18) show breakthrough at about 5 hours on stream under these conditions. The smaller crystallite SSZ-62 gives superior performance in this application.

What is claimed is:

1. A zeolite having the CHA crystal structure, a mole ratio greater than about 10 of an oxide of a first tetravalent element to an oxide of a second tetravalent element which is different from said first tetravalent element, trivalent element, pentavalent element or mixture thereof and having a crystallite size of 0.5 micron or less.

2. A zeolite having the CHA crystal structure, a mole ratio greater than about 10 of silicon oxide to aluminum oxide, and having a crystallite size of 0.5 micron or less.

3. A zeolite according to claim 2 wherein the mole ratio of silicon oxide to aluminum oxide is at least 30.

4. A zeolite according to claim 2 wherein the crystallite size is 0.1 micron or less.

5. A zeolite according to claim 1 wherein said zeolite is predominantly in the hydrogen form.

6. A zeolite according to claim 1 wherein said zeolite is substantially free of acidity.

7. A method of preparing an aluminosilicate crystalline material having the CHA crystal structure and a crystallite size of 0.5 micron or less, said method comprising contacting under crystallization conditions an aluminum hydroxide gel dried to about 50 wt. % $Al_2O_3$, precipitated silica with a water content of about 5–15 wt. % and a templating agent comprising a N,N,N-trimethyl-1-adamantammonium cation.

8. The method of claim 7 wherein the aluminum hydroxide has a particle density of less than about 1.0 g/cm³.

9. The method of claim 7 wherein the aluminum hydroxide has a particle size of less than about 40 microns.

10. The method of claim 7 wherein the aluminum hydroxide has an alkali content of less than about 0.12 wt. %.

11. A process for converting lower alcohols and other oxygenated hydrocarbons comprising contacting said lower alcohol or other oxygenated hydrocarbon under conditions to produce liquid products with a catalyst comprising a zeolite having the CHA crystal structure, a mole ratio greater than about 10 of silicon oxide to aluminum oxide and having a crystallite size of about 0.5 micron or less.

12. The process of claim 11 wherein the lower alcohol is methanol.

13. In a process for the reduction of oxides of nitrogen contained in a gas stream in the presence of oxygen wherein said process comprises contacting the gas stream with a zeolite, the improvement comprising using as the zeolite a zeolite having the CHA crystal structure, a mole ratio greater than about 10 of silicon oxide to aluminum oxide and having a crystallite size of 0.5 micron or less.

14. The process of claim 13 wherein said zeolite contains a metal or metal ions capable of catalyzing the reduction of the oxides of nitrogen.

15. The process of claim 14 wherein the metal is copper, cobalt or mixtures thereof.

16. The process of claim 14 wherein the gas stream is the exhaust stream of an internal combustion engine.

17. A process for producing dimethylamine comprising reacting methanol and/or dimethyl ether and ammonia in the gaseous phase in the presence of a catalyst comprising a zeolite having the CHA crystal structure, a mole ratio greater than about 10 of silicon oxide to aluminum oxide and having a crystallite size of 0.5 micron or less.

18. The process of claim 17 wherein the methanol and/or dimethylether and ammonia are present in amounts sufficient to provide a carbon/nitrogen ratio from about 0.2 to about 1.5.

19. The process of claim 17 conducted at a temperature of from about 250° C. to about 450° C.

20. In a process for separating gasses using a membrane containing a zeolite, the improvement comprising using a zeolite having the CHA crystal structure, a mole ratio greater than about 10 of silicon oxide to aluminum oxide and having a crystallite size of 0.5 micron or less.

21. The process of claim 20 wherein the process separates carbon dioxide from natural gas.

* * * * *